US00PP14914P2

(12) United States Plant Patent
Roberson

(10) Patent No.: US PP14,914 P2
(45) Date of Patent: Jun. 15, 2004

(54) LANTANA PLANT NAMED 'ROBMORNROG'

(50) Latin Name: *Lantana camara*
Varietal Denomination: Robmornrog

(76) Inventor: Robert J. Roberson, P.O. Box 210, Grain Valley, MO (US) 64029

( * ) Notice: Subject to any disclaimer, the term of this patent is extended or adjusted under 35 U.S.C. 154(b) by 0 days.

(21) Appl. No.: 10/666,278

(22) Filed: Sep. 17, 2003

(51) Int. Cl.[7] ..... A01H 5/00

(52) U.S. Cl. ..... Plt./227

(58) Field of Search ..... Plt./227

*Primary Examiner*—Kent Bell
(74) *Attorney, Agent, or Firm*—C. A. Whealy

(57) ABSTRACT

A new and distinct cultivar of Lantana plant named 'Robmornrog', characterized by its outwardly spreading and mounding plant habit; freely branching habit, dense and bushy appearance; freely flowering habit; and flowers that are golden yellow in color, then becoming orange and eventually dark pink.

1 Drawing Sheet

Botanical classification/cultivar designation: *Lantana camara* cultivar Robmornrog.

BACKGROUND OF THE INVENTION

The present Invention relates to a new and distinct cultivar of Lantana plant, botanically known as *Lantana camara,* and hereinafter referred to by the cultivar name Robmornrog.

The new Lantana is a product of a planned breeding program conducted by the Inventor in Grain Valley, Mo. The objective of the breeding program is to create mounded and freely branching Lantanas that are freely flowering.

The new Lantana originated from a self-pollination made by the Inventor in 1997 of the *Lantana camara* cultivar Robpatdes, disclosed in U.S. Plant Pat. No. 10,156. The new Lantana was selected as a single plant from the resulting progeny of the self-pollination by the Inventor in a controlled environment in 1998 in Grain Valley, Mo.

Asexual reproduction of the new cultivar by terminal cuttings taken in Grain Valley, Mo. since 1998, has shown that the unique features of this new Lantana are stable and reproduced true to type in successive generations.

SUMMARY OF THE INVENTION

Plants of the cultivar Robmornrog have not been observed under all possible environmental conditions. The phenotype may vary somewhat with variations in environment and culture such as temperature, light intensity and daylength without, however, any variance in genotype.

The following traits have been repeatedly observed and are determined to be the unique characteristics of 'Robmornrog'. These characteristics in combination distinguish 'Robmornrog' as a new and distinct cultivar:

1. Outwardly spreading and mounding plant habit.
2. Freely branching habit, dense and bushy appearance.
3. Freely flowering habit.
4. Flowers that are golden yellow in color, then becoming orange and eventually dark pink.

Plants of the new Lantana are most similar to plants of the parent cultivar. In side-by-side comparisons conducted in Grain Valley, Mo., plants of the new Lantana differed from plants of the cultivar Robpatdes in the following characteristics:

1. Plants of the new Lantana were smaller than plants of the cultivar Robpatdes.
2. Plants of the new Lantana had shorter internodes than plants of the cultivar Robpatdes.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Lantana.

The photograph at the top of the sheet comprises a side perspective view of a typical plant of 'Robmornrog' in a container.

The photograph at the bottom of the sheet comprises a close-up view of typical leaves and inflorescences of 'Robmornrog'.

DETAILED BOTANICAL DESCRIPTION

Plants used for the aforementioned photographs and following observations and measurements were grown for about 19 weeks in 15.25-cm containers and were pinched twice. Plants were grown in a polycarbonate-covered greenhouse in Lompoc, Calif. during the spring and summer with day temperatures ranging from 21 to 27° C., night temperatures ranging from 16 to 18° C., and light levels ranging from 5,000 to 9,000 foot-candles. In the following description, color references are made to The Royal Horticultural Society Colour Chart, 1995 Edition, except where general terms of ordinary dictionary significance are used.

Botanical classification: *Lantana camara* cultivar Robmornrog.

Parentage: Self-pollination of *Lantana camara* cultivar Robpatdes, disclosed in U.S. Plant Pat. No. 10,156.

Propagation:

*Type cutting.*—Terminal cuttings.

*Time to initiate roots, summer.*—About 10 days at 27° C.

*Time to initiate roots, winter.*—About 13 days at 27° C.

*Time to produce a rooted young plant, summer.*—About 37 days at 29° C.

*Time to produce a rooted young plant, winter.*—About 44 days at 24° C.

*Root description.*—Fine, fibrous; initially glaucous white becoming closer to 161D with development.

*Rooting habit.*—Freely branching.

Plant description:

*Form.*—Flowering subshrub; initially upright, then outwardly spreading and mounding. Freely branching; two lateral branches potentially forming at every node; pinching enhances lateral branch development; dense and busy growth habit.

*Plant height.*—About 20 cm.

*Plant diameter.*—About 30 to 44 cm.

*Vigor.*—Moderately vigorous growth habit.

*Lateral branches.*—Length: About 26 cm. Diameter: About 4 mm. Internode length: About 3 cm. Aspect: Initially upright, then outwardly bending to about 90° from vertical. Strength: Flexible, but strong. Texture: Sparsely pubescent. Color, immature: 144A. Color, mature: 165A.

*Foliage description.*—Arrangement: Opposite, simple. Length: About 7.4 cm. Width: About 4.8 cm. Shape: Elliptic. Apex: Acuminate. Base: Acute. Margin: Serrate. Texture, upper and lower surfaces: Coarse, rough, leathery; slightly pubescent. Venation pattern: Pinnate, arcuate. Fragrance: Pungent, spicy, pineapple-like. Color: Developing foliage, upper surface: 146A. Developing foliage, lower surface: 146B. Fully expanded foliage, upper surface: 147A. Fully expanded foliage, lower surface: 147B. Venation, upper surface: 146C. Venation, lower surface: 147D. Petiole length: About 1.9 cm. Petiole diameter: About 2 mm. Petiole color: 146A.

Flower description:

*Flower type and arrangement.*—Small solitary salver-form flowers arranged in axially umbels; flowers face mostly upward or outward. Umbels orientated about 45° from vertical.

*Quantity of flowers.*—Freely flowering with potentially two inflorescences developing per node. Typically about four open inflorescences per lateral branch in flower at one time with about 30 flowers per umbel.

*Natural flowering season.*—Spring until frost in the autumn; flowering continuous during this period.

*Flower longevity on the plant.*—About seven days. Flowers not persistent.

*Fragrance.*—Sweet, spicy, fruity.

*Inflorescence diameter.*—About 4.5 cm.

*Inflorescence height.*—About 2 cm.

*Flowers.*—Appearance: Flared trumpet, corolla fused, four-parted; flowers roughly rectangular in shape. Diameter: About 1.2 cm. Corolla tube length: About 1.8 cm. Corolla tube diameter, at base: About 2 mm.

*Flower buds* (*showing color*).—Length: About 8 mm. Diameter: Apex: About 3 mm. Base: About 1 mm. Shape: Elongate, oblong. Color: 44A, color becoming closer to 25A with development.

*Corolla.*—Arrangement: Single whorl of four petals, fused into flared trumpet. Petal length from throat: About 5 mm. Petal width: About 4.5 mm. Petal shape: Ovoid, irregular. Petal apex: Rounded. Petal margin: Entire. Petal texture: Smooth, velvety. Color: Petal, upper surface, when opening: 21A. Petal, lower surface, when opening: 21C. Petal, upper surface, fully opened: 32A, color becoming closer to 54A to 54B with development. Petal, lower surface, fully opened: 29C. Throat: 23A. Tube: 29C.

*Calyx.*—Arrangement: One single calyx tube per flower. Calyx length: About 3 mm. Calyx width: About 2 mm. Apex: Rounded to broadly acute. Texture: Pubescent. Color, upper and lower surfaces: 145B to 145C.

*Peduncles.*—Length: About 1.8 cm. Diameter: About 1.5 mm. Angle: About 45° from the stem. Strength: Flexible, but strong. Color: 146C.

*Pedicels.*—Length: Less than 1 mm. Diameter: Less than 1 mm. Color: Close to 146C.

*Reproductive organs.*—Stamens: Quantity/arrangement: Four per flower, adnate to floral tube. Anther shape: Ovoid. Anther length: Less than 1 mm. Anther color: 15A. Pollen amount: Scarce. Pollen color: 15A. Pistils: Quantity: One per flower. Pistil length: About 6 mm. Stigma shape: Bi-lobed. Stigma color: 145B. Style color: About 3.5 mm. Style color: 145C. Ovary color: 144A.

*Fruit/seed.*—Fruit and seed production has not been observed.

Disease/pest resistance: Plants of the new Lantana have not been noted to be resistant to pathogens or pests common to Lantana under commercial greenhouse conditions.

Weather tolerance: Plants of the new Lantana have been observed to be tolerant to rain, wind and temperatures ranging from 0 to 38° C.

It is claimed:

1. A new and distinct cultivar of Lantana plant named 'Robmornrog', as illustrated and described.

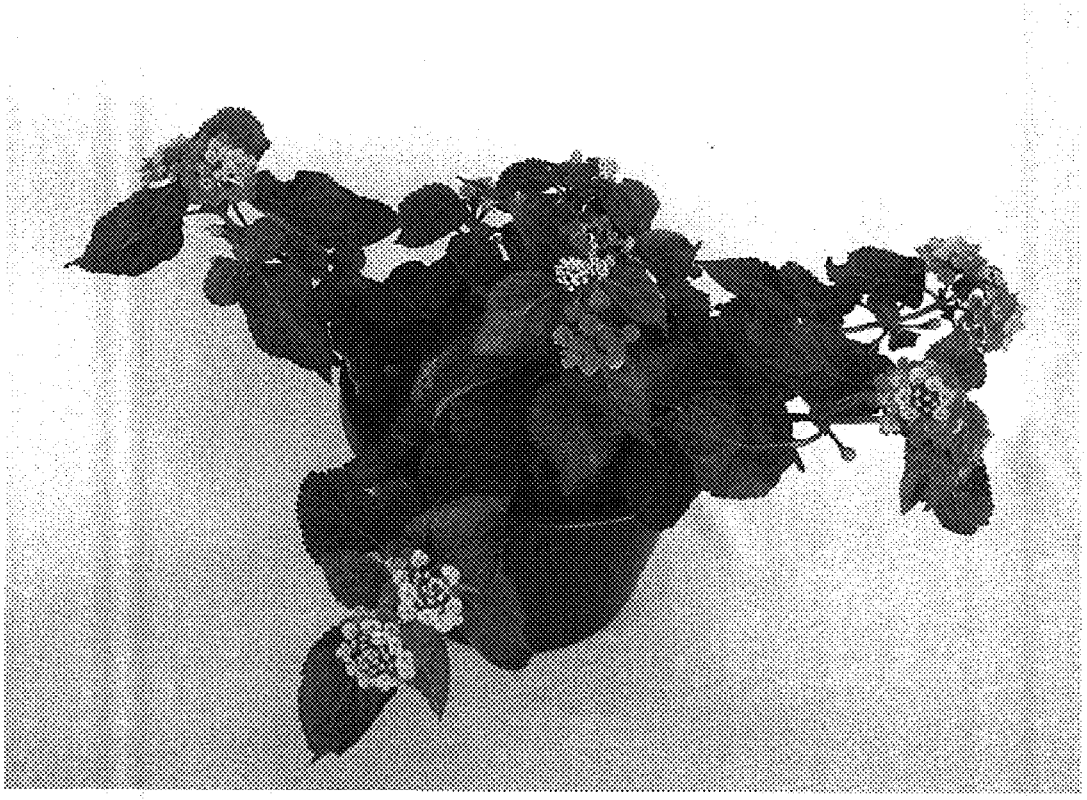
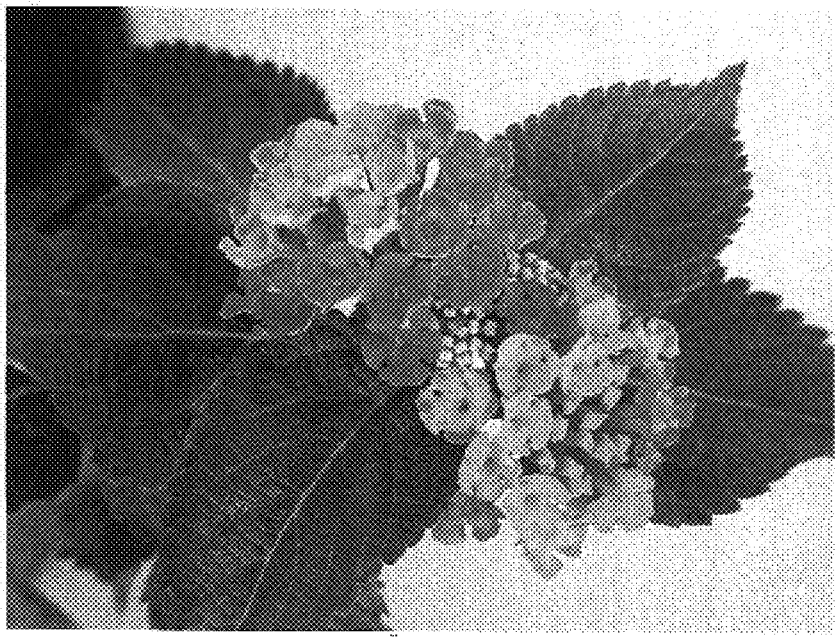

* * * * *